United States Patent [19]

Gerberich

[11] 4,390,730

[45] Jun. 28, 1983

[54] FORMALDEHYDE PRODUCTION

[75] Inventor: H. Robert Gerberich, Corpus Christi, Tex.

[73] Assignee: Celanese Corporation, New York, N.Y.

[21] Appl. No.: 287,384

[22] Filed: Jul. 27, 1981

[51] Int. Cl.$^3$ ............................................. C07C 45/052
[52] U.S. Cl. .................... 568/473; 568/472; 568/487; 252/461
[58] Field of Search ............... 568/473, 471, 472, 474, 568/487; 252/461

[56] References Cited

U.S. PATENT DOCUMENTS

| | | | |
|---|---|---|---|
| 1,735,763 | 11/1929 | Jaeger | 568/473 |
| 1,937,381 | 11/1933 | Bond | 568/471 |
| 3,334,143 | 8/1967 | Stiles | 568/473 |
| 3,728,398 | 4/1973 | Maux | 568/473 |
| 3,932,522 | 1/1976 | Seither et al. | 568/473 |
| 3,948,997 | 4/1976 | Howe et al. | 568/473 |
| 3,956,184 | 5/1976 | Krughkov | 568/473 |
| 3,959,383 | 5/1976 | Northeimer | 568/473 |
| 4,045,369 | 8/1977 | Cantaluppi | 252/432 |
| 4,076,754 | 2/1978 | Kiner et al. | 568/473 |
| 4,167,527 | 9/1979 | Neilsen | 568/473 |
| 4,242,235 | 12/1980 | Cogmon | 252/455 R |

*Primary Examiner*—Werren B. Lone
*Attorney, Agent, or Firm*—Linn I. Grim

[57] ABSTRACT

Lead-silver catalysts have been found to be useful in the production of formaldehyde by oxidative dehydrogenation of methanol vapor with an oxygen-containing gas at elevated temperatures.

20 Claims, No Drawings

FORMALDEHYDE PRODUCTION

FIELD OF INVENTION

This invention relates to the production of formaldehyde by the oxidative dehydrogenation of methanol using catalysts comprising lead and silver.

BACKGROUND OF THE INVENTION

Silver catalysts in the form of granules, gauze, wire turnings, crystals, and the like have been used for many years to produce formaldehyde by the oxidative dehydrogenation of methanol. Silver crystals are especially suitable for this purpose, since they are very selective and have little tendency to promote side reactions and the formation of by-products under reaction conditions which permit high overall yields.

Numerous prior art patents and publications describe the addition of small amounts of promoters to silver catalysts used in the production of formaldehyde from methanol. For example, U.S. Pat. No. 1,937,381, issued to Bond et al on Nov. 28, 1933 and assigned to du Pont, describes silver crystal oxidation catalysts containing promoters such as oxides of tungsten, vanadium, cerium, thorium, molybdenum, chromium, aluminum and zinc. Silver-cadmium alloy catalysts for the oxidative dehydrogenation of methanol are shown in U.S. Pat. No. 3,334,143, issued to Stiles on Aug. 1, 1960 and also assigned to du Pont. Silver containing up to 10% of an oxide of barium, strontium or calcium and up to 8% of an oxide of indium are taught as methanol oxidative dehydrogenation catalysts in U.S. Pat. No. 4,045,369, issued to Cantaluppi on Aug. 30, 1977 and assigned to S.A.E.S. Getters S.p.A. None of these patents suggest the use of lead in combination with silver as a methanol oxidative dehydrogenation catalyst.

Two literature articles from the Soviet Union, each entitled "Catalytic Properties of Silver Alloys in the Conversion of Methanol into Formaldehyde", also disclose various additives alloyed with silver for the oxidation of methanol to formaldehyde. The first is an abstract of *The Russian Journal of Physical Chemistry*, 45 (10), 1971 p. 1524. It discloses as methanol oxidative dehydrogenation catalysts silver alloys of aluminum, magnesium, copper, zinc, gallium, germanium, selenium, cadmium, indium, tin, antimony, tellurium and bismuth. The other publication is an article from *Tekh. Progr. Dostizh Nauki Khim. Prom.* 1973, p. 191–5 abstracted in Chemical Abstracts Vol. 81, 68971, 1974. It describes the same silver alloys as the first abstract except that the selenium and antimony alloys are not included. There is no mention of lead-silver catalysts in these articles. Of specific interest, however, is the description of the attempt to improve silver catalysts by adding tin and germanium (or the same group in the Periodic Table as lead) to improve the oxidative dehydrogenation of methanol to formaldehyde. Both of these additives to silver gave exceptionally poor results for formaldehyde production, compared to the use of silver alone.

A paper by Schwab entitled "Metal Electrons and Catalysts" in the *The Transactions of the Faraday Society* Vol. 42, 1946 p. 689–697, describes heterogeneous and homogeneous alloys of lead-silver, among other alloys. However, these catalysts were used to dehydrogenate formic acid to hydrogen and carbon dioxide, a reaction substantially different from the oxidative dehydrogenation of methanol to formaldehyde.

Another prior art patent, U.S. Pat. No. 3,948,997, issued Apr. 6, 1976 to Howe et al, describes a process for the vapor phase oxidation of $\alpha,\beta$-diols such as ethylene glycol to $\alpha,\beta$-diones such as glyoxal at elevated temperatures in the presence of a catalyst containing as essential constituents, one or more metals of Group Ib of the Periodic Table comprising copper, silver and gold, and one or more elements from Group IVa, comprising germanium, tin and lead, and Group Va, comprising nitrogen, phosphorus, arsenic, antimony and bismuth. However, there is no specific disclosure in this patent of a lead-silver catalyst, per se, nor is there any suggestion that any of the catalysts disclosed generically or specifically, could be used for the oxidative dehydrogenation of methanol to formaldehyde.

DETAILED DESCRIPTION OF THE INVENTION

The lead-silver catalysts used in the process of the present invention are readily prepared by impregnating lead onto silver. Preferably, the silver base used is silver crystals which are somewhat porous or irregular, e.g., silver crystals having particle sizes ranging from about 8 to about 40 mesh U.S. screen size (i.e. particles which will pass through a 8 mesh screen but which will be retained on a 40 mesh screen). A small amount of silver crystals having a mesh size larger than 8 mesh, i.e., up to about 10 weight percent of the total crystals, can be tolerated in the methanol conversion, but if the amount of large silver particles becomes excessive, the contact of methanol and oxygen with the silver crystals will be significantly decreased, resulting in lessened formaldehyde production. On the other hand, a small amount of silver crystals smaller than 40 mesh (again up to about 10 weight percent of the total catalyst) can be used in the methanol reaction. However, if a significant amount of smaller particles are present, an undesirable increase in the pressure drop across the catalyst bed may be observed. Particularly preferred are silver crystals having particle sizes ranging from about 20 to about 30 mesh (U.S. screen size).

One technique for preparing the catalysts of this invention involves impregnating silver crystals with a decomposable salt of lead, such as lead acetate, lead nitrate, or the like, and then decomposing the lead salt, for example by heat. Lead can also be applied to silver crystals by immersing the crystals in an organic or aqueous solution of a soluble lead salt and evaporating the solvent, preferably while stirring to obtain a more uniform distribution of lead on the silver crystals. Also a suspension or colloidal solution of a lead compound, prepared by any of the ordinary methods, may be flocculated while in contact with silver crystals to give a lead-silver catalyst.

The catalysts used in the process of this invention comprise silver and lead. The amount of lead in the catalyst can range from about 100 to about 150,000 parts per million, based on the total catalyst, and silver can comprise the remainder of the catalyst. The weight ratio of lead to silver on this basis can range from about 0.0001 to about 0.15. The preferred amount of lead in these catalysts can range from about 1000 to about 7000 parts per million, based on the total catalyst, with silver comprising the remainder of the catalyst. The preferred weight ratio of lead to silver can range from about 0.001 to about 0.007.

Lead-silver catalyst can also be prepared by depositing lead and silver on selected catalyst supports, such as silicon carbide or α-alumina, which do not detrimentally affect oxidative dehydrogenation of methanol to formaldehyde under the reaction conditions of the present invention. Such catalysts and processing conditions are described in copending application U.S. Ser. No. 287,385, filed July 27, 1981 in the names of H. R. Gerberich and E. T. Smith assigned to Celanese Corporation and filed concurrently with this application.

The process of this invention can be carried out in any conventional single stage or multiple stage methanol oxidation reactor at elevated temperatures. Individual reactors require facilities to hold a sufficient amount of oxidative dehydrogenation catalyst and to permit the methanol-oxygen mixture to pass over the catalyst to accomplish oxidative dehydrogenation. Downstream facilities to recover the formaldehyde product, normally in aqueous solution, are also required.

In carrying out the process of this invention, a feed mix of methanol and an oxygen-containing stream, such as pure oxygen, a mixture of oxygen and nitrogen, air, or other oxygen sources, i.e., one containing about 5 mol percent to about 100 mol percent of oxygen, is passed into a reactor containing catalyst comprising lead and silver and reacted at a temperature in the range from about 500° C. to about 700° C., preferably about 550° C. to about 650° C. Diluents such as steam and nitrogen, if desired, can be added to the methanol-oxygen mixture in amounts ranging from about 0.1 to about 10 mole of diluent per mole methanol in the feed, and preferably from about 0.75 to about 3 mole of dilute per mole methanol in the feed. The mole ratio of oxygen to methanol in the feed can range from about 0.15 to about 0.8, and preferably from about 0.2 to about 0.5. The space velocity of the feed entering the reactor generally will be maintained at from about 10 to about 150 reciprocal seconds, and preferably at from about 25 to about 80 reciprocal seconds.

Single stage operations, such as described above, although quite widely used to produce formaldehyde, suffer from the disadvantage that rather high amounts of unconverted methanol are contained in the product emerging from the catalyst bed. The presence of methanol in the exiting formaldehyde solution is undesirable since the methanol, generally, must be separated from the formaldehyde using expensive distillation facilities. However, the need for a separation step can be avoided by using a second oxidation stage of reaction. When carrying out a second oxidation, the effluent gases from the first stage reactor can be cooled, preferably below about 250° C., and mixed with an additional oxygen-containing stream, such as air. The use of such a two stage oxidation process is described in U.S. Pat. Nos. 2,462,413; 3,959,383; 3,987,107 and 4,076,754, among others. The effluent gas-oxygen mixture is then passed through a second stage catalytic oxidative dehydrogenation reactor containing sufficient catalyst to convert substantially all of the remaining unreacted methanol to formaldehyde. Temperatures in the range from about 550° C. to about 700° C., and preferably from about 600° C. to about 675° C., generally will be employed, while the space velocity of the gas in the second stage oxidation reactor generally will be maintained in the range of from about 10 to about 200 reciprocal seconds and preferably from about 30 to about 100 reciprocal seconds.

Any catalyst for the conversion of methanol to formaldehyde, and preferably a silver-containing catalyst, can be used in the second oxidation stage. Lead and silver catalysts, such as those used in the first stage oxidation reaction described above, can be used in the second stage as well. Conventionally used silver crystals, with or without other additives, can also be used.

The effluent gas emerging from the second stage can be passed through a cooler and then passed into the base of an absorber column. A stream of water may be introduced at the top of the absorber column in order to adjust the formaldehyde concentration in the aqueous formaldehyde product which is removed from the bottom of the column. The non-condensable gases entering the absorber are vented at the top of the column to an incinerator or to the atmosphere.

The advantages of the invention can be seen by reference to the following examples.

EXAMPLE 1

The unpromoted silver used in this and the following examples as a catalyst per se, as well as a base for the promoted catalysts of the present invention, was 20 to 30 U.S. screen mesh size silver crystals, electrolytic grade, 99.9% purity. To produce the promoted catalysts, an appropriate amount of lead acetate, antimony di-tartrate, or bismuth nitrate was impregnated on the silver crystals.

This was accomplished by first adding a solution of the desired metal salt to the silver crystals using an amount of solution just sufficient to cover the crystals. The liquid was then removed under vacuum, as a vapor, by heating. As an illustration, to prepare a silver catalyst containing 10,000 parts per million lead, lead acetate [$Pb(OAc)_2 \cdot 3H_2O$] in the amount of 0.46 gram was dissolved in demineralized water to make 5.8 ml of solution. This solution was poured onto 25 grams of silver crystals. The water solvent was then removed under vacuum at 100° C.

In preparing the antimony-containing catalysts, antimony di-tartrate, which is soluble in demineralized water, was poured on silver catalysts and the aqueous solvent removed by vaporization under vacuum at 100° C. In preparing the bismuth-containing catalysts, bismuth nitrate, dissolved in methanol containing a minor amount of concentrated nitric acid added to aid in the solubilization, was poured on silver crystals and the excess methanol removed by vaporization under vacuum at 100° C. After the catalysts were prepared, they were placed in the catalyst bed of the methanol oxidation unit.

EXAMPLES 2-16

The methanol oxidation unit used for these examples was an insulated, cylindrical reactor made of 316 stainless steel which is 7 inches long and has an internal diameter of ⅞ inch. In each run the reactor contained 17 grams of unpromoted silver catalyst. The catalyst bed was 0.5 inch deep. A thermocouple inserted into the catalyst bed was used to measure the reaction temperature. Air [7605 cc (STP)/min] was sparged into a heated vessel of liquid methanol. The gas leaving this vaporizer contains air to methanol mole ratio of 1.15 to 1.24. This vapor stream was mixed with a flow of pure nitrogen (1949 cc/min) and heated to 125° C. to avoid condensation. The mixture was fed to the methanol oxidation unit described above. Reaction was initiated by heating the catalyst bed with an electrical resistance winding which is on the external surface of the reactor. As soon as the methanol conversion reaction occurred as indicated by a sudden rise in temperature to 450° C. or above the timing of the run was begun. The conversions of methanol, which ranged from about 69 to about 76 percent, were collected by keeping the air and thus the oxygen in the feed stream constant and varying the oxygen-methanol ratio by controlling the methanol in the stream, with higher oxygen-methanol ratios yielding higher methanol conversions. Once the reaction, which is exothermic, was initiated, the temperature was permitted to reach its own level, with no external heat being added to the reaction and no heat being deliberately absorbed by heat exchangers while the reaction is continuing, although an undetermined amount of heat may of course have escaped into the surroundings through the reactor walls. The product stream is analyzed by gas chromatography for mole percent nitrogen, oxygen, methanol, carbon dioxide, carbon monoxide, hydrogen and methyl formate. Data were collected for the period of 5 to 20 hours after initiation of the reaction. The conditions of the reaction were:

catalyst temperature-545°-612° C.
reaction pressure-5.8 psig
oxygen conversion-99.5 percent
space velocity-51 sec$^{-1}$ Table I sets out the results of the methanol oxidative dehydrogenation to formaldehyde using the unpromoted silver crystals for comparison with the promoted catalysts under the conditions set forth above. The table indicates catalyst temperatures used in the reaction, length of run, conversions of methanol to total products, and the efficiencies of converted methanol to carbon dioxide ($CO_2$), methyl formate (MeFo) and formaldehyde (HCHO).

TABLE I-continued

UNPROMOTED PURE SILVER CRYSTALS - (CONTROL CASES)

| Examples | Catalyst Temp, °C. | Air/Methanol Mole Ratio | Efficiency, % | | | Length of Run, Hours | Conv. % |
|---|---|---|---|---|---|---|---|
| | | | $CO_2$ | MeFo | HCHO | | |
| 14 | 582 | 1.19 | 6.66 | 1.68 | 91.7 | 16 | 71.8 |
| 15 | 585 | 1.18 | 7.01 | 1.32 | 91.7 | 15 | 72.0 |
| 16 | 545 | 1.24 | 7.51 | 1.31 | 91.2 | 14 | 72.7 |

The average values of the 15 experiments in Table I and the standard deviations are:

| temperature, °C. | 582 ± 16 |
|---|---|
| formaldehyde efficiency, % | 91.1 ± 0.6 |
| methyl formate efficiency, % | 1.48 ± 0.18 |
| carbon dioxide efficiency, % | 7.34 ± 0.40 |
| methanol conversion, % | 72.0 ± 1.7 |
| air/methanol, mole ratio | 1.19 ± .025 |

The term "standard deviation" as used in the foregoing and the following examples is well known in statistics. (See: Box, Hunter, and Hunter, "Statistics for Experimenters," John Wiley & Sons, New York, 1978, p. 40.)

EXAMPLES 17-29

Table II sets out the results of the methanol oxidative dehydrogenation to formaldehyde in the same equipment as used in Examples 2-16 and the same reaction conditions except for slight variations in reaction temperature and reactor feed compositions using promoted

TABLE II

PURE SILVER CRYSTALS PROMOTED WITH LEAD AND BISMUTH

| Examples | Bi ppm[a] | Pb ppm[a] | Air/Methanol Mole Ratio | Catalyst Temp, °C. | Efficiency, % | | | Length of Run, Hours | Conv. % |
|---|---|---|---|---|---|---|---|---|---|
| | | | | | $CO_2$ | MeFo | HCHO | | |
| 17 | 0 | 1000 | 1.20 | 580 | 6.93 | 1.28 | 91.8 | 14 | 74.3 |
| 18 | 0 | 3000 | 1.20 | 586 | 6.34 | 1.41 | 92.2 | 27 | 72.1 |
| 19 | 0 | 5000 | 1.21 | 591 | 6.23 | 1.32 | 92.5 | 20 | 72.2 |
| 20 | 0 | 7000 | 1.21 | 586 | 6.31 | 1.39 | 92.3 | 19 | 72.3 |
| 21 | 1000 | 0 | 1.30 | 590 | 6.32 | 1.16 | 92.5 | 12 | 73.2 |
| 22 | 10000 | 0 | 1.34 | 597 | 6.88 | .93 | 92.2 | 21 | 72.7 |
| 23 | 3000 | 0 | 1.31 | 582 | 6.64 | 1.18 | 92.2 | 18 | 72.8 |
| 24 | 300 | 0 | 1.25 | 593 | 6.75 | .94 | 92.3 | 23 | 73.7 |
| 25 | 1800 | 0 | 1.28 | 608 | 6.08 | .68 | 93.2 | 20 | 72.6 |
| 26 | 600 | 0 | 1.26 | 593 | 6.51 | .91 | 92.6 | 16 | 72.7 |
| 27 | 1400 | 0 | 1.24 | 588 | 6.17 | .99 | 92.8 | 23 | 72.8 |
| 28 | 100 | 0 | 1.29 | 595 | 6.84 | .93 | 92.2 | 18 | 75.4 |
| 29 | 30000 | 0 | 1.34 | 588 | 8.14 | .90 | 91.0 | 40 | 68.0 |

[a]Parts per million of metal added

TABLE I

UNPROMOTED PURE SILVER CRYSTALS - (CONTROL CASES)

| Examples | Catalyst Temp, °C. | Air/Methanol Mole Ratio | Efficiency, % | | | Length of Run, Hours | Conv. % |
|---|---|---|---|---|---|---|---|
| | | | $CO_2$ | MeFo | HCHO | | |
| 2 | 552 | 1.23 | 7.49 | 1.46 | 91.0 | 15 | 73.4 |
| 3 | 578 | 1.18 | 7.21 | 1.48 | 91.3 | 12 | 74.2 |
| 4 | 583 | 1.17 | 6.86 | 1.58 | 91.6 | 5 | 71.7 |
| 5 | 595 | 1.18 | 6.99 | 1.36 | 91.3 | 4 | 72.9 |
| 6 | 576 | 1.17 | 7.92 | 1.61 | 90.0 | 15 | 72.8 |
| 7 | 612 | 1.15 | 7.82 | 1.45 | 90.5 | 4 | 67.1 |
| 8 | 587 | 1.16 | 7.59 | 1.71 | 90.5 | 11 | 69.4 |
| 9 | 590 | 1.20 | 8.08 | 1.89 | 90.0 | 14 | 72.2 |
| 10 | 589 | 1.22 | 7.32 | 1.39 | 91.3 | 15 | 72.7 |
| 11 | 583 | 1.19 | 7.13 | 1.30 | 91.6 | 14 | 72.2 |
| 12 | 583 | 1.21 | 7.21 | 1.37 | 91.4 | 12 | 73.3 |
| 13 | 595 | 1.19 | 7.39 | 1.26 | 91.4 | 20 | 71.3 | silver catalysts, specifically silver crystals containing lead or bismuth as promotor.

Comparing the results of Examples 17-20 using lead on silver catalysts with those results of Examples 2-16 using unpromoted silver crystals, the lead on silver catalysts provide higher efficiencies of 91.8-92.5 percent formaldehyde at methanol conversions of 72.3-74.3 percent, at temperatures of 580° to 591° C. and lengths of run of 14 to 27 hours while the unpromoted silver catalysts provide efficiencies having a standard deviation of 91.1±0.6 percent (range 90.5-91.7 percent) at methanol conversions of 72.0±1.7 percent (range 70.3-73.7 percent) at temperatures of 545° to 612° C. and lengths of run of 4 to 20 hours. The results obtained with lead and silver are better than those obtained using silver alone, and are technically and commercially significant since they indicate that in a commercial unit carrying out the oxidative dehydrogenation of methanol to formaldehyde, it is possible to obtain at least at 1% improvement in formaldehyde efficiency at methanol conversions of upwards of 70% by employing a silver catalyst promoted with a small amount of lead rather than conventional unpromoted silver. Such an improvement translates into a substantial economic advantage in terms of increased formaldehyde yields.

As brought out previously, the recorded temperatures are those resulting after the initiation of reaction without any external temperature control. Within the range reported in the examples, the temperature of reaction is not believed to affect formaldehyde efficiency at a set methanol conversion level. The varying values of length of run reported in these and the other examples disclosed herein are also believed not to affect the results in terms of formaldehyde efficiency since these values are considerably below the minimum catalyst age at which the activity of the catalyst is adversely affected.

The same types of improvements obtained with lead are also obtained by using bismuth on silver, as illustrated in Examples 21–28, instead of unpromoted silver. However, the use of bismuth on silver results in a significant loss of bismuth from the catalyst during the course of the reaction. Moreover, the use of bismuth as a promoter is also undesirable because formaldehyde made with this catalyst tends to be contaminated with bismuth, and bismuth tends to deposit in the reaction system.

EXAMPLES 30–32

Antimony on pure silver crystal catalysts prepared as described in Example 1 were evaluated in the same equipment as used for Examples 2–16 and under the same conditions except for slight variations in reaction temperatures and reactor feed compositions. These examples can be compared with the control Examples 2–16. The results of Examples 30–32 are no better than the control Examples 2–16 and not as good as the lead Examples 17–20. Table III illustrates these results.

the support. Water was removed by heating at 100° C. under vacuum. When bismuth nitrate is used in combination with lead and/or silver nitrate, a small amount of nitric acid is used to aid in dissolving the bismuth nitrate.

The silver on silicon carbide catalyst was prepared in the same manner as the catalyst comprising lead and silver, but without utilizing any lead salt.

The methanol oxidation unit used for these examples is an insulated, cylindrical reactor made of 316 stainless steel which is 7 inches long and has an internal diameter of ⅜ inch. In each run, the catalyst was employed in a bed 1.0 inch deep. A thermocouple inserted into the catalyst bed was used to measure the reaction temperature. Air [7605 cc (STP)/min] was sparged into a heated vessel of liquid methanol. The gas leaving the vaporizer contains air to methanol ratios as indicated in Table IV. This vapor stream was mixed with a flow of pure nitrogen (1949 cc/min), heated to 125° C. to avoid condensation, and fed to the methanol oxidation unit described above. Reaction was initiated by heating the catalyst bed with an electric resistance winding which is on the external surface of the reactor. As soon as the methanol conversion reaction was initiated, as indicated by a sudden rise in temperature to 450° C. or above, the timing of the run was begun. The conversions of methanol obtained were at levels ranging from 60.1 percent to 75.7 percent and the product stream was analyzed by gas chromatography for mole percent nitrogen, oxygen, methanol, carbon monoxide, carbon dioxide, hydrogen, and methyl formate. The conditions of the reaction were:

catalyst temperature-529°–659° C.
reaction pressure-5.8 psig
oxygen conversion-99.5 percent
space velocity-26 sec$^{-1}$ The silicon carbide carrier was produced from 3/16 inch spheres, in some examples these spheres were used as the carrier without modification. In other examples, utilizing smaller catalyst particles, the 3/16 inch spheres are crushed and sieved to achieve the desired screen mesh size (U.S. screen size). The 3/16 inch silicon car-

TABLE III

PURE SILVER CRYSTALS PROMOTED WITH ANTIMONY

| Examples | Sb ppm[a] | Catalyst Temp, °C. | Air/Methanol Mole Ratio | Efficiency, % | | | Length of Run, Hours | Conv. % |
|---|---|---|---|---|---|---|---|---|
| | | | | CO$_2$ | MeFo | HCHO | | |
| 30 | 1000 | 588 | 1.22 | 8.46 | 1.41 | 90.1 | 20 | 71.2 |
| 31 | 5000 | 612 | 1.29 | 8.18 | .84 | 91.0 | 26 | 71.9 |
| 32 | 15000 | 593 | 1.22 | 7.93 | 1.14 | 90.9 | 24 | 71.3 |

[a]Parts per million of metal added

EXAMPLES 33–82

These examples illustrate the use of supported catalysts in which the carrier is silicon carbide.

An amount of silicon carbide carrier was wetted with the salt solution containing the total amount of metallic elements desired in the final catalyst. The aqueous solvent was removed by heating at 100° C. under vacuum.

As an illustration, to prepare a silver-lead on silicon carbide catalyst containing 13.0 weight percent metals with a lead to silver ratio of 0.048 by weight, silver nitrate (2.25 grams) and lead nitrate (0.11 gram) were dissolved in demineralized water (total solution volume of 5.2 ml). This solution was poured onto 10 grams of bide spheres have a surface area of less than 1 m$^2$/g. The silicon carbide carriers used contain approximately 60–78% silicon carbide, 4–11% aluminum oxide (Al$_2$O$_3$) and 14–26% SiO$_2$, and it was found that any differences in carrier composition within these ranges did not affect the results obtained. Table IV sets out the results of methanol oxidative dehydrogenation to formaldehyde using varying amounts of silver and lead-silver on various silicon carbide carriers of varying sizes. The table indicates catalyst temperatures used in the reaction, length of run, conversions of methanol to total products, and the efficiencies of converted methanol to carbon dioxide (CO$_2$), carbon monoxide (CO), methyl formate (MeFo) and formaldehyde (HCHO).

TABLE IV

SILICON CARBIDE SUPPORTED CATALYSTS

| Example | Support Mesh or Size | Carrier | Ag Wt % | Pb Wt % | Bi Wt % | Air/Methanol Mole Ratio | Length of Runs, Hours | Temp °C. | Conv. % | HCHO % | CO₂ % | CO % | MeFo % |
|---|---|---|---|---|---|---|---|---|---|---|---|---|---|
| 33 | 3/16″ | 1 | 9.1 | — | — | 1.13 | 15 | 561 | 61.5 | 86.1 | 9.8 | 1.8 | 2.4 |
| 34 | 3/16″ | 1 | 16.1 | — | — | 1.15 | 7 | 548 | 60.2 | 83.4 | 11.0 | 3.4 | 2.2 |
| 35 | 14–28 | 1 | 9.1 | — | — | 1.28 | 38 | 640 | 60.1 | 87.2 | 9.9 | 2.7 | 0.2 |
| 36 | 14–28 | 1 | 9.1 | — | — | 1.15 | 18 | 580 | 67.3 | 91.5 | 6.6 | 0.2 | 1.1 |
| 37 | 14–28 | 1 | 9.1 | — | — | 1.23 | 42 | 596 | 71.7 | 91.3 | 7.1 | 0.6 | 1.0 |
| 38 | 14–28 | 1 | 13 | — | — | 1.22 | 28 | 566 | 72.3 | 91.6 | 6.8 | 0.5 | 1.1 |
| 39 | 14–28 | 1 | 13 | — | — | 1.09 | 34 | 553 | 66.1 | 92.4 | 6.2 | 0 | 1.4 |
| 40 | 14–28 | 1 | 13.0 | — | — | 1.15 | 28 | 577 | 67.6 | 90.9 | 7.24 | 0 | 1.87 |
| 41 | 14–28 | 1 | 13.0 | — | — | 1.22 | 40 | 595 | 72.3 | 90.4 | 7.65 | 0.33 | 1.60 |
| 42 | 4–8 | 2 | 4.6 | 1.85 | .93 | 1.25 | 13 | 625 | 52.7 | 46.0 | 8.1 | 45.2 | 0.6 |
| 43 | 4–8 | 2 | 16.3 | 1.63 | .41 | 1.30 | 15 | 632 | 62.5 | 82.4 | 8.23 | 8.59 | 0.78 |
| 44 | 4–8 | 2 | 4.8 | — | — | 1.20 | 12 | 549 | 66.9 | 79.5 | 7.6 | 11.8 | 1.0 |
| 45 | 4–8 | 2 | 12.7 | 0.35 | — | 1.32 | 19 | 620 | 71.6 | 88.8 | 7.5 | 2.9 | 0.8 |
| 46 | 4–8 | 2 | 12.7 | 0.35 | — | 1.15 | 39 | 557 | 66.4 | 90.2 | 6.8 | 0.9 | 2.1 |
| 47 | 14–28 | 1 | 12.4 | 0.61 | — | 1.27 | 39 | 530 | 74.1 | 92.9 | 5.9 | 0.0 | 1.1 |
| 48 | 14–28 | 1 | 12.4 | 0.61 | — | 1.09 | 62 | 529 | 65.8 | 93.5 | 5.0 | 0.0 | 1.4 |
| 49 | 14–28 | 1 | 12.4 | 0.61 | — | 1.22 | 75 | 543 | 72.3 | 92.6 | 5.9 | 0.3 | 1.2 |
| 50 | 14–28 | 1 | 12.4 | 0.61 | — | 1.27 | 42 | 598 | 71.4 | 92.4 | 6.7 | 0.0 | 0.9 |
| 51 | 14–28 | 2 | 12.4 | 0.61 | — | 1.17 | 17 | 580 | 66.3 | 92.2 | 6.3 | 0.0 | 1.5 |
| 52 | 14–28 | 2 | 12.4 | 0.61 | — | 1.26 | 33 | 601 | 72.2 | 92.0 | 6.9 | 0.0 | 1.1 |
| 53 | 14–28 | 3 | 12.4 | 0.61 | — | 1.19 | 18 | 610 | 65.7 | 92.7 | 6.0 | 0.0 | 1.3 |
| 54 | 14–28 | 3 | 12.4 | 0.61 | — | 1.28 | 30 | 623 | 72.2 | 92.4 | 6.6 | 0.0 | 1.0 |
| 55 | 14–28 | 1 | 15.17 | 1.45 | — | 1.24 | 21 | 659 | 64.4 | 92.5 | 6.9 | 0.0 | 0.6 |
| 56 | 14–28 | 1 | 15.17 | 1.45 | — | 1.33 | 39 | 636 | 72.5 | 91.5 | 7.6 | 0.0 | 0.9 |
| 57 | 14–28 | 1 | 12.7 | 0.30 | — | 1.24 | 19 | 574 | 72.2 | 93.3 | 5.7 | 0.0 | 1.0 |
| 58 | 14–28 | 1 | 12.7 | 0.30 | — | 1.12 | 28 | 558 | 67.5 | 93.5 | 5.1 | 0.0 | 1.4 |
| 59 | 14–28 | 1 | 12.7 | 0.30 | — | 1.19 | 42 | 562 | 71.3 | 93.0 | 5.6 | 0.0 | 1.4 |
| 60 | 28–35 | 1 | 12.9 | 0.16 | — | 1.10 | 18 | 566 | 66.1 | 93.5 | 5.1 | 0.0 | 1.4 |
| 61 | 28–35 | 1 | 12.9 | 0.16 | — | 1.21 | 27 | 591 | 72.4 | 93.1 | 5.8 | 0.0 | 1.1 |
| 62[b] | 14–28 | 1 | 12.4 | .61 | — | 1.26 | 41 | 604 | 72.4 | 92.0 | 6.24 | 0 | 1.74 |
| 63[b] | 14–28 | 1 | 12.4 | .61 | — | 1.34 | 50 | 608 | 75.7 | 91.8 | 6.61 | 0 | 1.56 |
| 64 | 14–28 | 1 | 12.4 | .61 | — | 1.16 | 12 | 561 | 59.4 | 94.4 | 4.86 | 0 | 0.73 |
| 65 | 14–28 | 1 | 12.4 | .61 | — | 1.22 | 32 | 608 | 65.2 | 94.1 | 5.15 | 0 | 0.76 |
| 66 | 14–28 | 1 | 12.4 | .61 | — | 1.26 | 49 | 601 | 71.7 | 93.5 | 5.56 | 0 | 0.91 |
| 67 | 14–28 | 1 | 12.4 | .61 | — | 1.22 | 14 | 624 | 66.4 | 93.8 | 5.6 | 0 | 0.7 |
| 68 | 13–18 | 1 | 12.4 | .61 | — | 1.29 | 37 | 622 | 74.9 | 92.9 | 6.2 | 0 | 0.9 |
| 69[a] | 14–28 | 1 | 12.4 | .61 | — | 1.17 | 15 | 588 | 65.5 | 93.4 | 5.27 | 0. | 1.34 |
| 70[a] | 14–28 | 1 | 12.4 | .61 | — | 1.26 | 43 | 607 | 71.4 | 93.5 | 5.51 | 0 | 1.02 |
| 71 | 14–28 | 1 | 4.7 | .66 | .09 | 1.22 | 23 | 632 | 66.5 | 91.7 | 5.31 | 2.01 | 0.98 |
| 72 | 14–28 | 1 | 4.7 | .66 | .09 | 1.28 | 47 | 619 | 70.3 | 91.6 | 5.58 | 1.75 | 1.09 |
| 73 | 14–28 | 1 | 16.3 | 1.2 | .81 | 1.25 | 17 | 644 | 64.3 | 93.1 | 5.20 | 1.21 | 0.48 |
| 74 | 14–28 | 1 | 16.3 | 1.2 | .81 | 1.33 | 38 | 651 | 69.8 | 93.3 | 5.52 | 0.68 | 0.53 |
| 75 | 14–28 | 1 | 13.0 | .05 | — | 1.25 | 23 | 590 | 72.7 | 91.3 | 7.09 | 0 | 1.64 |
| 76 | 14–28 | 1 | 13.0 | .05 | — | 1.12 | 42 | 561 | 65.7 | 91.2 | 6.53 | 0 | 2.26 |
| 77 | 14–28 | 1 | 12.7 | — | .30 | 1.28 | 18 | 624 | 63.1 | 90.9 | 6.6 | 1.7 | 0.8 |
| 78 | 14–28 | 1 | 12.3 | .43 | .43 | 1.25 | 28 | 604 | 65.5 | 92.5 | 5.8 | 0.4 | 1.3 |
| 79 | 14–28 | 1 | 12.3 | .43 | .43 | 1.27 | 47 | 632 | 67.7 | 93.5 | 5.6 | 0.0 | 0.9 |
| 80 | 14–28 | 1 | 12.3 | .43 | .43 | 1.29 | 63 | 608 | 69.7 | 92.7 | 6.0 | 0.0 | 1.3 |
| 81 | 14–28 | 1 | 12.6 | .43 | .04 | 1.31 | 34 | 616 | 72.2 | 92.7 | 6.2 | 0.0 | 1.1 |
| 82 | 14–28 | 1 | 15.9 | — | .75 | 1.29 | 20 | 628 | 64.5 | 90.6 | 6.2 | 2.5 | 0.7 |

Carrier Major Composition
1 SiO₂-16.5%, Al₂O₃-5.86%, SiC-75.9% -Surface area 0.27 m²/g square meters per gram
2 SiO₂-14.5%, Al₂O₃-4.38%, SiC-77.78% - Surface area 0.20 m²/g square meters per gram
3 SiO₂-26.37%, Al₂O₃-11.42%, SiC-59.1% - Surface area 0.31 m²/g square meters per gram
[a]Catalyst calcined in air at 585° C. for 20 hours before reaction
[b]Catalyst calcined in air at 260° C. for 24 hours, then at 650° C. for 24 hours before reaction Certain results from Table IV of the oxidative dehydrogenation of methanol over catalysts containing lead and silver on silicon carbide are compared in Table V below with those obtained catalysts containing silver only on silicon carbide at the same methanol conversion levels of ~72% and ~66–67%.

TABLE V

COMPARISON OF Ag/SILICON CARBIDE WITH Ag—Pb/SILICON CARBIDE

| Example | Carrier Size Mesh | Ag % | % Pb | % Methanol Conversion | % Formaldehyde Efficiency |
|---|---|---|---|---|---|
| ~72% METHANOL CONVERSION | | | | | |
| 38 | 14–28 | 13 | 0 | 72.3 | 91.6 |
| 41 | 14–28 | 13 | 0 | 72.3 | 90.4 |
| 49 | 14–28 | 12.4 | 0.61 | 72.3 | 92.6 |
| 50 | 14–28 | 12.4 | 0.61 | 71.4 | 92.4 |
| 52 | 14–28 | 12.4 | 0.61 | 72.2 | 92.0 |
| 54 | 14–28 | 12.4 | 0.61 | 72.2 | 92.4 |
| 57 | 14–28 | 12.7 | 0.30 | 72.2 | 93.3 |
| 59 | 14–28 | 12.7 | 0.30 | 71.3 | 93.0 |
| 61 | 28–35 | 12.9 | 0.16 | 72.4 | 93.1 |
| 62 | 14–28 | 12.4 | 0.61 | 72.4 | 92.0 |
| 66 | 14–28 | 12.4 | 0.61 | 71.7 | 93.5 |
| 70 | 14–28 | 12.4 | 0.61 | 71.4 | 93.5 |
| 75 | 14–28 | 13.0 | 0.05 | 72.7 | 91.3 |
| ~66–67% METHANOL CONVERSION | | | | | |
| 39 | 14–28 | 13 | 0 | 66.1 | 92.4 |

TABLE V-continued
COMPARISON OF Ag/SILICON CARBIDE WITH Ag—Pb/SILICON CARBIDE

| Example | Carrier Size Mesh | Ag % | % Pb | % Methanol Conversion | % Formaldehyde Efficiency |
|---|---|---|---|---|---|
| 40 | 14–28 | 13 | 0 | 67.6 | 90.9 |
| 48 | 14–28 | 12.4 | 0.61 | 65.8 | 93.5 |
| 51 | 14–28 | 12.4 | 0.61 | 66.3 | 92.2 |
| 53 | 14–28 | 12.4 | 0.61 | 65.7 | 92.7 |
| 58 | 14–28 | 12.7 | 0.30 | 67.5 | 93.5 |
| 60 | 28–35 | 12.9 | 0.16 | 66.1 | 93.5 |
| 65 | 14–28 | 12.4 | 0.61 | 65.2 | 94.1 |
| 67 | 14–28 | 12.4 | 0.61 | 66.4 | 93.8 |
| 69 | 14–28 | 12.4 | 0.61 | 65.5 | 93.4 |
| 76 | 14–28 | 13.0 | 0.05 | 65.7 | 91.2 |

Although at the ~72% conversion level, Example 38 employing only silver on the silicon carbide support yields a formaldehyde efficiency of 91.6%, almost as good as that obtained in Example 62, viz. 92.0% which utilized a catalyst containing silver and 0.61% of lead, and at the ~66–67% conversion level, Example 39 employing a lead-free supported catalyst yielded a formaldehyde efficiency comparable to that of Examples 51 and 53 which utilized a catalyst containing 0.61 of lead in addition to silver, the results shown in this table as a whole indicate that the supported catalysts comprising silver and lead in most cases yield better results in terms of formaldehyde yield and methanol utilization than are obtained with lead-free supported silver catalysts. It should also be noted that Example 75 at the 72% conversion level and Example 76 at the ~66–67% conversion level both of which employed a catalyst containing 0.05% lead, yielded lower efficiencies than the other examples utilizing higher amounts of lead in the catalyst. This indicates that the lead content must be increased above 0.05 weight percent of the catalyst or 500 parts per million to obtain the improved results for formaldehyde efficiencies.

The results shown in Table IV also indicate that bismuth-silver without lead on silicon carbide (Examples 77 and 82) did not provide the improved formaldehyde efficiencies over the use of supported silver catalysts containing no bismuth. The presence of a small amount of bismuth in combination with lead and silver on a silicon carbide support (Examples 71–74) does not raise the efficiencies of formaldehyde from methanol over those obtained with supported lead and silver catalysts. The catalyst of Example 42 using 1.85 weight percent lead in combination with 4.6 weight percent silver and bismuth at 0.93 weight percent on a silicon carbide support (4–8 mesh), provides an unsatisfactory formaldehyde efficiency of 46% at 52.7% methanol conversion level.

EXAMPLES 83–100B

Various sizes of a carrier identified as Celite I, which has a composition of 75% $SiO_2$ and 10% $Al_2O_3$ and a surface area of 19 $m^2/g$, were used as the carrier for the catalysts employed in these examples. The catalysts contained varying amounts of silver alone or lead and silver and were used in the methanol oxidation to formaldehyde in the same unit under the same conditions, except for slight variations in temperature, as used for Examples 33–82, at a catalyst depth of 1.0 inch. Table VI sets out the results obtained, using the same symbols as used in Table IV.

TABLE VI
75% $SiO_2$ 10% $Al_2O_3$ SUPPORTED CATALYSTS

| Example | Support Mesh Size or mm | Ag Wt % | Other Metals % | Air/Methanol Mole Ratio | Length of Runs Hours | Temp °C. | Methanol Conv. | HCHO % | $CO_2$ % | CO % | MeFo % |
|---|---|---|---|---|---|---|---|---|---|---|---|
| 83 | ⅛" | 9.1 | — | 1.14 | 21 | 596 | 60.4 | 86.9 | 9.3 | 2.2 | 1.6 |
| 84 | ⅛" | 9.1 | — | 1.06 | 27 | 581 | 56.7 | 87.6 | 9.0 | 1.3 | 2.1 |
| 85 | 6–10 | 16.7 | — | 1.13 | 6 | 607 | 61.0 | 89.4 | 7.7 | 2.2 | 0.7 |
| 86 | 6–10 | 16.7 | — | 1.21 | 20 | 628 | 63.6 | 89.0 | 7.6 | 2.7 | 0.5 |
| 87 | 6–10 | 16.7 | — | 1.21 | 35 | 603 | 64.8 | 89.6 | 7.9 | 1.8 | 0.8 |
| 88 | ⅛" | 16.7 | — | 1.14 | 10 | 571 | 58.7 | 81.0 | 8.6 | 8.7 | 1.6 |
| 89 | 8–14 | 16.7 | — | 1.14 | 9 | 568 | 63.4 | 89.8 | 8.3 | 0.9 | 1.0 |
| 90 | 14–28 | 16.7 | — | 1.16 | 13 | 578 | 64.6 | 90.1 | 7.9 | 1.2 | 0.8 |
| 91 | 14–28 | 16.7 | — | 1.18 | 38 | 597 | 63.5 | 90.9 | 7.0 | 1.9 | 0.2 |
| 92 | 14–28 | 9.1 | — | 1.19 | 12 | 606 | 64.4 | 90.2 | 7.6 | 1.9 | 0.3 |
| 93 | 14–28 | 9.1 | — | 1.18 | 24 | 583 | 63.8 | 89.5 | 7.6 | 1.7 | 1.2 |
| 94 | 14–28 | 28.6 | — | 1.15 | 16 | 571 | 65.7 | 90.2 | 8.0 | 1.0 | 0.9 |
| 95 | 14–28 | 28.6 | — | 1.15 | 26 | 590 | 66.8 | 90.3 | 7.7 | 1.2 | 0.7 |
| 96 | 14–28 | 28.6 | — | 1.30 | 40 | 601 | 73.2 | 88.9 | 8.8 | 1.7 | 0.5 |
| 97 | 14–28 | 4.8 | — | 1.25 | 8 | 638 | 63.6 | 89.2 | 7.6 | 3.2 | 0.0 |
| 98 | 14–28 | 13.0 | — | 1.15 | 16 | 615 | 64.0 | 90.9 | 7.4 | 0.9 | 0.8 |
| 99 | 14–28 | 12.4 | 0.6 (Pb) | 1.27 | 23 | 667 | 62.3 | 91.0 | 7.6 | 0.6 | 0.8 |
| 100 | 14–28 | 12.9 | 0.17 (Pb) | 1.22 | 17 | 558 | 66.6 | 92.7 | 5.7 | 0.9 | 0.8 |
| 100A | 14–28 | 12.9 | 0.17 (Pb) | 1.20 | 20 | 533 | 66.4 | 92.3 | 5.9 | 0.8 | 0.9 |
| 100B | 14–28 | 12.9 | 0.17 (Pb) | 1.31 | 44 | 587 | 71.7 | 91.4 | 6.5 | 1.5 | 0.6 |

It should be noted that in Table VI, examples 100–100B, describing catalysts comprising 0.17 weight percent lead and 12.9 weight percent silver on $SiO_2$-$Al_2O_3$ supports, better results in regard to formaldehyde efficiencies were obtained compared to Example 98, using 13 weight percent silver on $SiO_2$-$Al_2O_3$ support. Example 99, describing the use of 0.6 weight percent lead and 12.4 weight percent silver on $SiO_2$-$Al_2O_3$ support, resulted in an exceptionally high temperature of 667° to yield a formaldehyde efficiency of 91 percent at 62.3 percent methanol conversion. This relatively high temperature appears to be an anomaly in view of the lower temperature reached in obtaining the formaldehyde efficiencies indicated in the catalysts of the other examples in Table VI of silver alone and silver and lead on $SiO_2$-$Al_2O_3$ support. Furthermore, the result of Example 99 is not consistent with the results obtained using other catalysts comprising lead and silver on $SiO_2$-$Al_2O_3$ supports, since the result is not significantly better than the results of Example 98 (13 weight percent silver on $SiO_2$-$Al_2O_3$).

EXAMPLES 101-107

Using an α-alumina carrier (87% Al$_2$O$_3$ and 11.7% SiO$_2$) having a surface area of less than 1.0 m$^2$/g as a support for silver and the combination of lead and silver, catalysts were prepared using the procedure set forth in Examples 33-82. The methanol oxidation unit and conditions employed were the same as these used in Examples 33-82, except for slight variations in temperature. Table VII sets out the results using the same symbols as were used for Table IV.

TABLE VII

α-ALUMINA SUPPORTED CATALYSTS

| Example | Support Mesh Size or Inches | Ag Wt % | Pb Wt % | Air/Methanol Mole Ratio | Length of Runs Hours | Temp °C. | Methanol Conv. % | HCHO % | CO$_2$ % | CO % | MeFo % |
|---|---|---|---|---|---|---|---|---|---|---|---|
| 101 | 3/16" | 9.1 | — | 1.16 | 16 | 563 | 63 | 85.0 | 11.1 | 1.8 | 2.0 |
| 102 | 3/16" | 9.1 | — | 1.15 | 6 | 586 | 62 | 84.8 | 10.5 | 3.1 | 1.7 |
| 103 | 14-28 | 13 | — | 1.20 | 7 | 570 | 72.2 | 90.3 | 7.89 | 0 | 1.8 |
| 104 | 14-28 | 13 | — | 1.28 | 20 | 587 | 76.8 | 90.2 | 8.3 | 0 | 1.5 |
| 105 | 14-28 | 13 | — | 1.07 | 27 | 571 | 66.0 | 90.6 | 7.01 | 0.4 | 1.9 |
| 106 | 14-28 | 12.6 | 0.43 | 1.17 | 19 | 562 | 67.1 | 92.4 | 5.9 | 0 | 1.67 |
| 107 | 14-28 | 12.6 | 0.43 | 1.25 | 44 | 583 | 72 | 92.1 | 6.3 | 0 | 1.63 |

The results of Table VII indicate that the catalysts comprising lead and silver on α-alumina (14-28 mesh) provided improved results compared to the catalysts of silver alone on α-alumina (14-28 mesh) in the oxidative-dehydrogenation of methanol to formaldehyde. Thus, the lead-silver catalysts of Examples 106-107 yielded formaldehyde efficiencies of 92.1-92.4 percent at methanol conversions of 67.1-72 percent while the lead-free silver catalysts of Examples 103-105 provided lower formaldehyde efficiencies of 90.2-90.6 at methanol conversions of 66-76.8 percent.

Based on the results of Examples 33 to 107, it can be concluded that in a commercial unit for the oxidative dehydrogenation of methanol to formaldehyde utilizing a catalyst comprising silver on a support, and methanol conversions of 60 to 75%, the employment of a small amount of lead with the silver makes it possible to increase the formaldehyde efficiency at a set methanol conversion by at least 1%. This is a significant economic advantage in terms of the increased formaldehyde yield obtained.

What is claimed is:

1. In a process for the production of formaldehyde by oxidative dehydrogenation of methanol vapor with oxygen at elevated temperatures, the improvement which comprises passing a mixture of methanol and an oxygen-containing gas over a catalyst comprising silver and lead.

2. The process of claim 1 wherein said catalyst has a lead to silver weight ratio ranging from about 0.0001 to about 0.15.

3. The process of claim 1 wherein said catalyst has a lead to silver weight ratio ranging from about 0.001 to about 0.007.

4. The process of claim 2 wherein the silver is in the form of silver crystals.

5. The process of claim 3 wherein the silver is in the form of silver crystals.

6. The process of claim 4 wherein the size of the silver crystals ranges from about 8 to about 40 mesh U.S. screen size.

7. The process of claim 5 wherein the size of the silver crystals ranges from about 8 to about 40 mesh U.S. screen size.

8. The process of claim 4 wherein the size of the silver crystals ranges from about 20 to about 30 mesh U.S. screen size.

9. The process of claim 5 wherein the size of the silver crystals ranges from about 20 to about 30 mesh U.S. screen size.

10. In a two stage process for the production of formaldehyde by oxidative dehydrogenation of methanol vapor with oxygen at elevated temperatures, the improvement which comprises passing a mixing of methanol and an oxygen-containing gas in the first stage over a catalyst comprising silver and lead and passing the effluent gases from said first stage and additional oxygen-containing gas into a second stage over a silver-containing catalyst.

11. The process of claim 10 wherein said catalyst in said first stage comprises silver and lead where the weight ratio of lead to silver ranges from about 0.0001 to about 0.15.

12. The process of claim 10 wherein said catalyst in said first stage comprises silver and lead where the weight ratio of lead to silver ranges from about 0.001 to about 0.007.

13. The process of claim 11 wherein said catalyst in said first stage ranges from about 8 to about 40 mesh U.S. screen size.

14. The process of claim 12 wherein said catalyst in said first stage ranges from about 8 to about 40 mesh U.S. screen size.

15. The process of claim 11 wherein said catalyst in said first stage comprises lead deposited on silver crystals ranging from about 20 to about 30 mesh U.S. screen size.

16. The process of claim 12 wherein said catalyst in said first stage comprises lead deposited on silver crystals and ranging from about 20 to 30 mesh U.S. screen size.

17. The process of claim 15 wherein the catalyst in said second stage is the same as in said first stage.

18. The process of claim 16 wherein the catalyst in said second stage is the same as in said first stage.

19. The process of claim 15 wherein the catalyst in said second stage comprises silver crystals ranging from about 20 to about 30 mesh U.S. screen size.

20. The process of claim 16 wherein the catalyst in said second stage comprises silver crystals ranging from about 20 to about 30 mesh U.S. screen size.

* * * * *